United States Patent [19]
Connolly et al.

[11] Patent Number: 5,563,929
[45] Date of Patent: Oct. 8, 1996

[54] ON-LINE MONITOR FOR PARTICULATE ANALYTE IN A MOVING LIQUID

[75] Inventors: Dennis J. Connolly; John M. Rackley, both of Alliance; Charles C. Stauffer, Beloit, all of Ohio

[73] Assignee: The Electric Power Research Institute, Palo Alto, Calif.

[21] Appl. No.: 471,611

[22] Filed: Jun. 6, 1995

Related U.S. Application Data

[63] Continuation of Ser. No. 198,315, Feb. 18, 1994, abandoned.

[51] Int. Cl.$^6$ .................................................. G01N 21/35
[52] U.S. Cl. ................................. 378/51; 378/45; 378/53
[58] Field of Search .................... 378/51, 44, 45, 378/46, 47, 50, 53, 54, 57, 70, 83, 86, 88, 89; 250/343, 373, 339.12; 356/246, 410, 440

[56] References Cited

U.S. PATENT DOCUMENTS

| | | |
|---|---|---|
| H188 | 1/1987 | Thomson . |
| 3,547,540 | 12/1970 | Shigemoto ............................ 356/28 |
| 3,790,760 | 2/1974 | Stiller ................................ 235/92 PC |
| 3,925,661 | 12/1975 | Carr-Brion ........................... 250/272 |
| 4,140,395 | 2/1979 | Kreikebaum ......................... 356/366 |
| 4,167,870 | 9/1979 | Haas ..................................... 73/194 |
| 4,182,957 | 1/1980 | Forster et al. ....................... 378/51 X |
| 4,264,330 | 4/1981 | Schmidt ............................... 23/230 R |
| 4,532,026 | 7/1985 | Fries ..................................... 208/164 |
| 4,561,777 | 12/1985 | Radziemski ......................... 356/318 |
| 4,711,571 | 12/1987 | Schuman ............................. 356/311 |
| 4,801,805 | 1/1989 | Butler et al. ......................... 250/343 |
| 4,924,097 | 5/1990 | Browner et al. ..................... 250/343 |
| 4,990,780 | 2/1991 | Lee et al. ............................. 250/343 |
| 5,008,906 | 4/1991 | Reichwein ........................... 378/51 X |
| 5,065,416 | 11/1991 | Laurila et al. ....................... 378/51 X |
| 5,107,125 | 4/1992 | Powell ................................ 250/483.1 |

(List continued on next page.)

FOREIGN PATENT DOCUMENTS 0024129  2/1987  Japan ...................................... 356/440

OTHER PUBLICATIONS

Yuasa, et al, J. of Nuclear Science and Technology, 17(7):564–566 Jul. 1980.
Jaklevic, J. Amer. Chem. Soc., 15(6):687–89(?), Jun. 1981.

*Primary Examiner*—David P. Porta
*Attorney, Agent, or Firm*—Phillips, Moore, Lempio & Finley

[57] ABSTRACT

The present invention relates to an apparatus and a method for the determination of the concentration level of a particulate analyte in a moving liquid, said apparatus comprising:

valve means for diverting a quantifiable portion of the liquid through an analysis chamber, wherein the chamber itself comprises:

valve inlet means for introducing the liquid to the analysis chamber, concentrating means for accumulating the particulate analyte present in the liquid, valve outlet means for the removing liquid having a reduced concentration of analyte;

valve inlet means for introducing an anhydrous gas into said analysis chamber, valve outlet means for removing the inert gas and a major portion of the liquid present in analysis chamber, electromagnetic radiation generating means positioned in non contacting proximity to said concentration means, detecting means for detecting an electromagnetic radiation parameter of the analyte located in non-contacting proximity to said concentration means; and flow sensor means for measuring the liquid flow within the analysis chamber. The present invention is particularly useful to concentrate and to determine particulate iron compounds and/or sulfur compounds in a moving aqueous stream. This method is particularly useful in power generation plants to determine the extent of corrosion of the metal components on a real-time basis.

20 Claims, 3 Drawing Sheets

U.S. PATENT DOCUMENTS

| | | | |
|---|---|---|---|
| 5,133,901 | 7/1992 | Peterson et al. | 252/626 |
| 5,164,604 | 11/1992 | Blair et al. | 250/574 |
| 5,200,064 | 4/1993 | Russ et al. | 356/440 X |
| 5,225,679 | 7/1993 | Clarke et al. | 250/339.12 X |

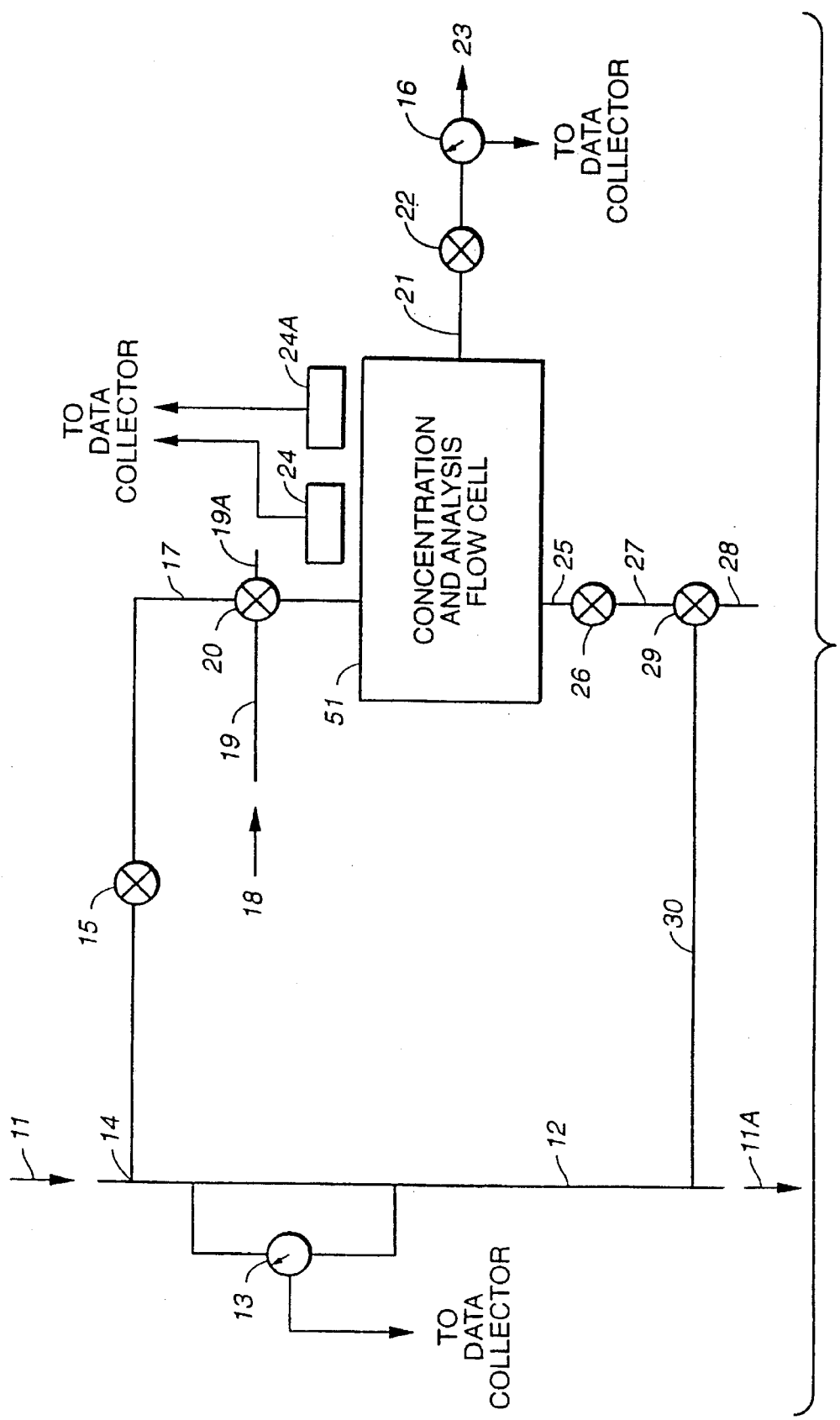
*FIG._1*

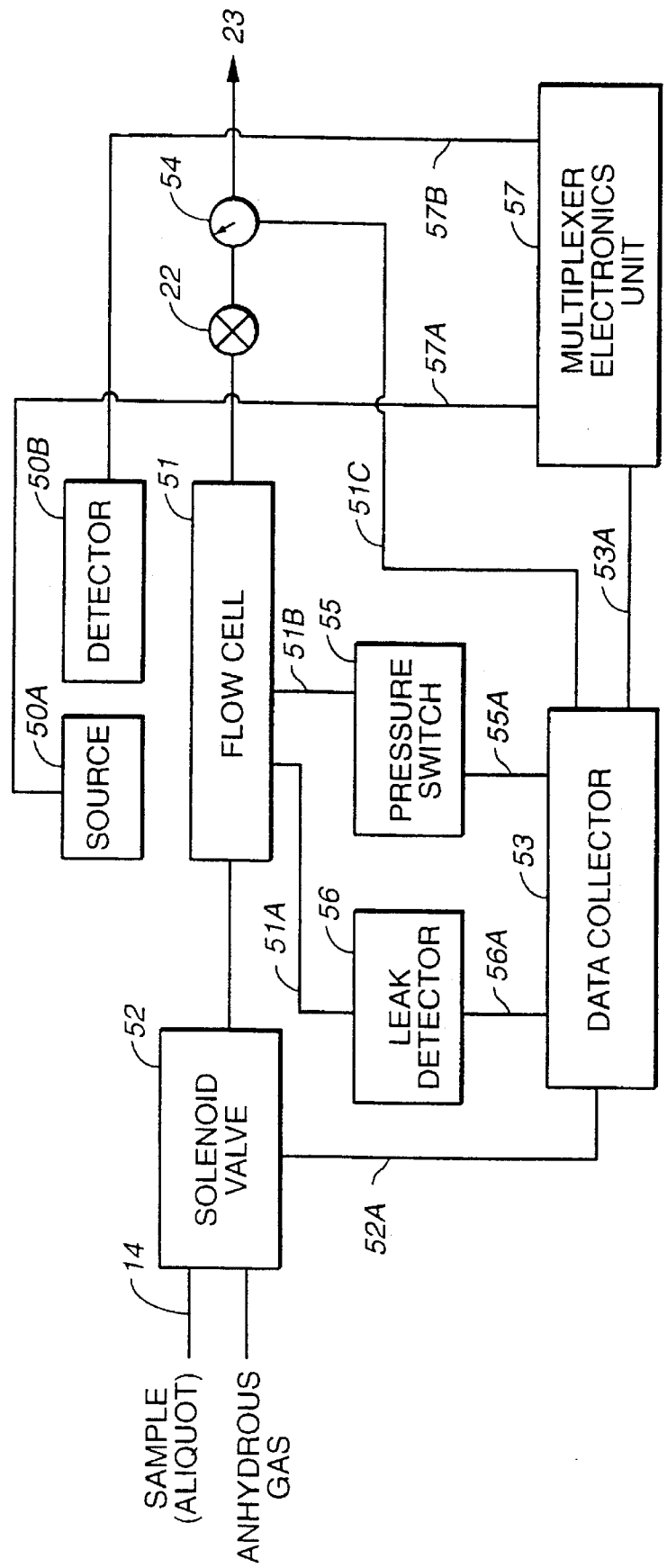
FIG._2

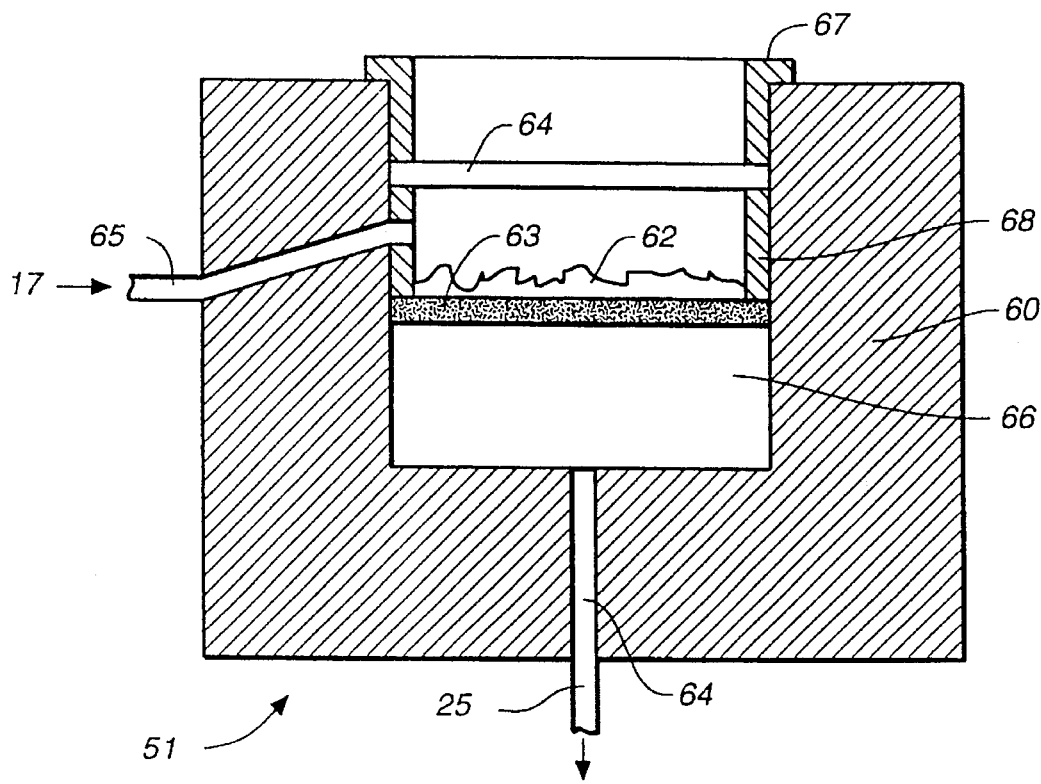
FIG._3
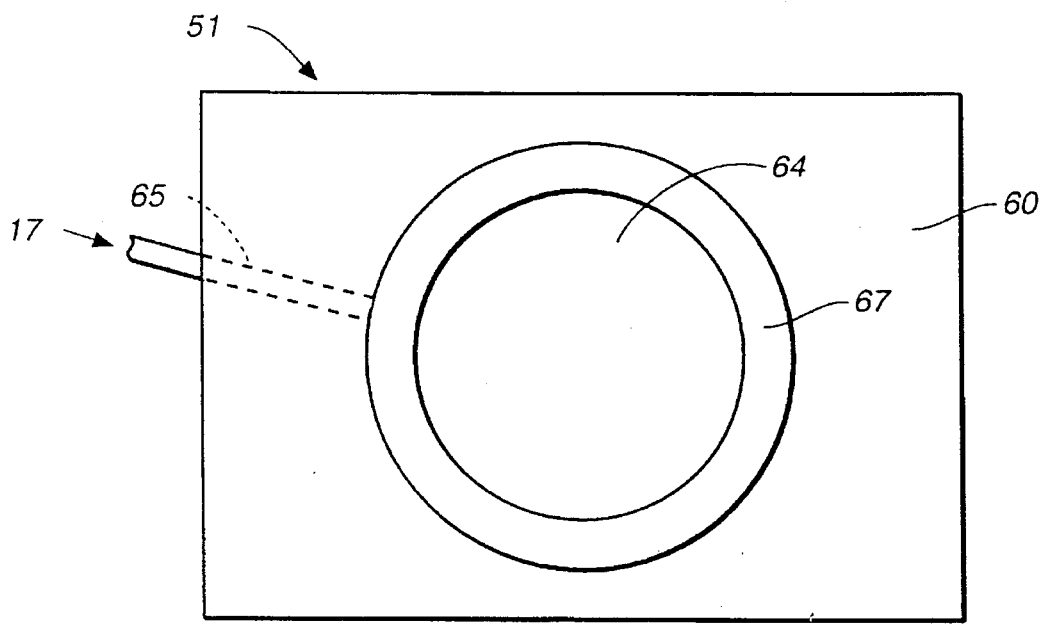
FIG._4

ON-LINE MONITOR FOR PARTICULATE ANALYTE IN A MOVING LIQUID

This is a continuation of application of Ser. No. 08/198,315 filed on Feb. 18, 1994 now abandoned.

BACKGROUND OF THE INVENTION

1. Field of the Invention

The present invention concerns an apparatus and a method for the concentration and the determination of the concentration level of a particulate analyte (e.g., iron or sulfur compounds) in a moving liquid.

2. Description of Related Art

Techniques for monitoring and analysis of corrosion products have gone through several evolutionary stages in recent years. Sample collection by filtration of corrosion products is now supplemented by backup ion exchange membranes to capture both filterable as well as dissolved material. Analytical methods have progressed from quick and rough estimation using comparison charts, through element specific instrumental analysis, via atomic adsorption (AA) or inductively coupled plasma (ICP), to the rapid, multi-element methods of x-ray fluorescence spectroscopy.

Despite these refinements, corrosion product monitoring techniques continue to have the significant limitation that each individual analysis represents an integrated sample which, at best, gives only average concentration values for any particular sample collection period, which period may range from minutes to hours or days. The final analytical result lacks a distinction between: 1) a case of a steady rate of corrosion product transport, and 2) one by which transient instances of high corrosion product concentration account for the majority of the collection sample. This latter information, when it is available, would be useful to correlate in time with controllable parameters of the operating source of the particulate, i.e. the operating plant.

The present invention accomplishes the desired objectives by increasing the rate of sampling and analysis of corrosion products from hours or days to minutes to provide a more complete and more accurate time profile of the behavior of particulate analytes in a moving liquid.

SUMMARY OF THE INVENTION

The present invention relates to an apparatus and a method for the determination of the concentration level of a particulate analyte in a moving liquid, the apparatus comprising:

valve means for diverting a quantifiable portion of the liquid through an analysis chamber, wherein said chamber itself comprises:

valve inlet means for introducing the liquid to the analysis chamber, concentrating means for accumulating the particulate analyte present in the liquid, valve outlet means for the removing the liquid leaving the concentrated analyte in the analysis chamber;

valve inlet means for introducing an anhydrous gas into the analysis chamber, valve outlet means for removing the gas and a portion of the liquid present in analysis chamber leaving concentrated particulate analyte within the analysis chamber, electromagnetic radiation generating means for producing quantifiable electromagnetic radiation signals positioned in non contacting proximity to the concentrated particulate analyte, detecting means for detecting an electromagnetic radiation parameter of the analyte located in non-contacting proximity to the concentrated particulate analyte; and flow sensor means for measuring the liquid flow within the analysis chamber.

In another aspect, the present invention relates to a method for the determination of the concentration level of a particulate analyte in a moving liquid, the method comprising:

a. obtaining an apparatus itself comprising:

valve means for diverting a quantifiable portion of the liquid through an analysis chamber, wherein the chamber itself comprises:

valve inlet means for introducing the liquid to the analysis chamber, concentrating means for accumulating the particulate analyte present in the liquid, valve outlet means for removing the liquid having a reduced concentration of analyte;

valve inlet means for introducing an anhydrous gas into the analysis chamber, valve outlet means for removing the anhydrous gas and a portion of the liquid present in the analysis chamber, electromagnetic radiation generating means positioned in non contacting proximity to the concentration means, detecting means for detecting of an electromagnetic radiation parameter located in non-contacting proximity to said concentration means, and optional flow sensor means for measuring the liquid flow within the analysis chamber;

b. diverting a quantifiable portion of the moving liquid into the analysis chamber;

c. concentrating the particulate analyte for a period of time using the concentration means for concentrating the particulate;

d. contacting the concentrated particulate analyte with a gas via the valve inlet means to further remove the liquid present in the analysis chamber via the valve outlet;

e. irradiating the concentrated particulate analyte in the analysis chamber with electromagnetic radiation;

f. detecting and quantifying an electromagnetic radiation parameter of the particulate analyte; and g. correlating the electromagnetic radiation parameter of the particulate analyte with a predetermined scale of values to determine the concentration of the particulate analyte in the moving liquid.

The main components of the present invention are an X-ray probe (source and detector), a flow totalizer, and a valve switching mechanism to control liquid flow through a specially designed sample flow cell. The monitoring process is controlled by a computer program as it cycles between two modes of operation: sample collection mode during which particulates accumulate and are concentrated in the sample chamber, and sample measurement mode during which analyte measurement takes place.

The apparatus and method are particularly useful to determine and monitor the rate of corrosion in the cooling system of electric power plants.

BRIEF DESCRIPTION OF THE DRAWINGS

FIG. 1 is a schematic representation of the concentration and analysis apparatus.

FIG. 2 is a schematic representation of a specific embodiment of the component parts of the concentration and analysis of the moving liquid.

FIG. 3 is a schematic cross sectional representation of the flow cell.

FIG. 4 is a schematic cross sectional top view of the flow cell.

DETAILED DESCRIPTION OF THE INVENTION AND PREFERRED EMBODIMENTS

Definitions

As used herein:

"Analyte" refers to any quantifiable element or compound found a particulate contained in a moving liquid. Pure elements or corrosion products are preferred. These include, for example, iron oxide, iron hydroxide, sodium bisulfite, sodium sulfite, sodium sulfate, and the like. Analytes such as iron compounds or sulfur compounds are preferred.

"Liquid" refers to water, and the usual organic liquid which encountered in a flowing system, and combinations thereof.

"Organic liquid" refers to common liquids and/or solvents, such as alcohols, butanol, DMF, DMAC, hydrocarbons, benzene, toluene, FREONS®, etc.

Referring to FIG. 1 and FIG. 3, the broadest aspects of the present invention are described. The liquid 11 to be analyzed for particulate content is moving in pipe 12 at a quantifiable rate of flow (as determined by flow meter 13). A separate pipe 14 connects with pipe 12 having a valve 15 and flow totalizer 16 so that one or more quantifiable aliquots of the flow of liquid in pipe 12 is obtained.

The moving aliquot of liquid enters the concentration and analysis cell 51 via pipe 17.

The concentration and analysis cell 51 is constructed of materials conventional in the art. It is important to remove liquid, if present, from the sample because the liquid interferes with the analysis of the particulates. In one embodiment, removal of liquid is accomplished by switching away from liquid sample and introducing an anhydrous gas 18 via pipe 19 using valve 20 to control the rate and quantity of the gas. The liquid is removed from chamber 62 via pipe 21 at optional valve 22 and discarded (at 23). The concentration of the particulate is accomplished under conditions that the liquid is removed while retaining essentially all of the particulate of the aliquot sample in cell 51 for analysis.

The concentrated particulate sample in cell 51 is then subjected to electromagnetic radiation from source 24, and the appropriate signal generated by the concentrated sample are detected by detector 24A.

After analysis, the next aliquot is introduced into cell 51 and the particulate is concentrated and analyzed as is described above. Thus a constantly increasing amount of particulate is analyzed.

Alternatively, after analysis, cell 51 is cleaned to remove the concentrated sample. The analyzed sample is removed mechanically or by flushing using an appropriate cleaning solution which is introduced via pipe 19 and valve 20 (optionally a 4-way valve) and is removed via pipe 25 and valve 26. The cleaning solution is either discarded or disposed of via pipe 27 and pipe 28 or is diverted via valve 29 to pipe 30 to become part of the moving liquid 11A in pipe 12. The analysis chamber is then available for collecting the next aliquot of particulate.

The rate and volume of moving liquid, the volume of the aliquot sample, the identity and quantity of particulate in the concentrated sample are determined by input of these factors into a data collection and manipulatory system. The quantity of particulate per unit volume of the flowing liquid over time is then determined.

A specific embodiment of the present invention targets the compounds of two elements: iron and sulfur. In this regard, the monitor may be configured as a single channel or a multi-channel system. The schematic drawings in FIGS. 1 and 2 show the component parts of a typical analysis.

The present invention is based on the X-ray fluorescence (XRF) technique of elemental analysis. Since iron and sulfur levels in most sample streams of interest are usually below the detection limit of direct XRF analysis, a concentration mechanism is required. The new monitor utilizes an XRF probe with a specially designed sample collection cell to continuously measure the accumulation of particulate iron on a membrane filter. The monitor may contain a second parallel system (separate collection cell and separate X-ray probe) to similarly monitor sulfur-containing particulates in the sample stream. The iron and sulfur channels may be operated simultaneously or separately.

The main components of the monitor are as follows:

a. an X-ray probe (source 50A and detector 50B in FIG. 2);

b. a sample flow cell (51 in FIG. 2 and FIG. 3);

c. a valve switching system (52 in FIG. 2);

d. a flow totalizer (54 in FIG. 2); and e. a control and data acquisition system (53 in FIG. 2).

The X-ray probe consists of a sealed radioisotope excitation source 50A and a proportional counter type fluorescence detector 50B. The radioisotope for the iron probe contains curium-244, and the sulfur probe contains iron-55. The probes are designed such that the radioisotope is shielded with a shutter mechanism, which is open only when the probe body is properly set into a measurement position over the sample cell. In this manner, samples are continuously irradiated. However, data acquisition from the detector is initiated either manually or via a computer program when a measurement is desired.

Referring now specifically to FIGS. 2, 3 and 4, sample flow cell 51 has a body 60 which is usually constructed from DELRIN®, a polyacetal type polymer (available from the DuPont Co., Wilmington, Del.). The body 60 contains a sample chamber 62 sandwiched between a sample filter 63 (about 0.45 micron) and a KAPTON® (a polyimide available from the DuPont Co.) X-ray window 64. Sample inlet 65 is on the side and sample flow is directed approximately parallel to the surface of the membrane filter 63. Sample liquid drain 64 is directly below the filter support 64. Retainer 67 holds X-ray window 64 in place in body 60. Retainer 68 separates X-ray window 64 and filter 63.

The X-ray probe 50A fits over the top of the flow cell 51 such that the radioisotope source and detector are aligned with the KAPTON® window and less than one inch from the surface of the filter 63. Both the X-ray source 50A and detector 50B and the flow cell 51 are contained in a closed cell box during operation.

Since water, even in small thicknesses or concentrations, severely attenuates the X-ray signals, the method was developed to enhance the sensitivity of the monitor by periodically evacuating the sample chamber, and flushing the chamber with an anhydrous gas, e.g. nitrogen or helium. Thus, the monitor alternates between two modes during operation: a) sample collection mode during which the sample is flowing and particulates are depositing on the filter, and b) sample measurement mode during which the sample is temporarily diverted from the flow cell, water is evacuated from the sample chamber 62, and a dry gas e.g. helium, flush proceeds while the measurement takes place. An electrically actuated solenoid valve (52 in FIG. 2) sets the operating mode, and is connected electrically to software control (53 in FIG. 2) via line 52A. The valves automatically switch between modes on a predetermined schedule. The dry gas flush is selected from dry air, helium, nitrogen, or combinations thereof. A gas pressure of about 10 to 50 psig, preferably 35 to 40 psig, is used. Within seconds, the sample on the filter has about 90% of the water removed, and more than 95% of the water is removed in about 1 to 5 minutes.

In the sample collection mode, a flow totalizer 54 (in FIG. 2) continuously monitors the liquid flow through the filter 63. Flow totalizer 54 is connected with piping to flow cell 51 via line 23 and to data collection 53 via line 54A. This measurement is then used in conjunction with the subsequent X-ray analysis to determine the analyte concentration of the sample moving stream 11.

Control of data and data acquisition (53 in FIG. 2) from the monitor are usually handled by a 486 type personal computer (PC) using a LAB-PC (National Instruments) data acquisition card for interface and LabVIEWS for Windows (National Instruments) software. This package distributes the necessary electronic signals to control the sequencing of valve settings and maintains the scheduling between the two modes of operation. Triggering signals are provided to initiate acquisition of X-ray and flow data at appropriate times through a monitoring period. Input includes X-ray analytical data and flow totals. Data processing includes conversion of raw X-ray data (counts) to elemental mass, combining mass and flow values to concentrations, displaying current and historical measurements, as well as a variety of graphing and other data formatting activities.

The monitor also provides sensing and control capability for protection against overpressurization (switch 55 in FIG. 2 which is connected electrically to flow cell 51 via line 51B and to data collector 53 via line 55A). Leak detection (56 in FIG. 2 which is connected electrically to flow cell 51 via line 51A and to data collector 53 via line 56A). These components divert sample flow and alert the user in these eventualities.

The sensitivity of the monitor is a function of three parameters: the sample flow rate, the time between measurements, and the fluorescence efficiency of the element being analyzed. For iron, at a liquid flow rate of 300 milliliters per minute, and for 5 minute sample collection times between measurements, the sensitivity of the measurement is about 10,000 parts per billion down to about 1 part per billion.

This method is useful to determine iron levels on the filter of between about 1 and 10,000 ppb, preferably between about 1000 and 1.

The following Examples are presented for the purposes of explaining and describing the invention. They are not to be construed to be limiting in any manner.

EXAMPLE 1

IRON DETERMINATION (a) A sample stream containing iron bearing particulates is directed through the filter chamber. Flow continues for sufficient time to build up measurable iron sample on the filter. This time of collection will vary depending on the iron content of the stream. For example, if the X-ray analyzer is capable of detecting changes of the order of one microgram of iron on the filter, then for a stream containing one part per billion iron the flow must continue until at least one liter of sample fluid has passed through the filter. Once this predetermined flow time has elapsed, the sample valve switches to direct sample away from the flow cell and to introduce air (or other anhydrous gas) into the flow cell thereby purging the cell of liquid. While the purge continues, X-ray fluorescence data are collected for a predetermined time. The iron fluorescence intensity (in counts per second) detected is the related to a previously performed iron calibration as appropriate for the X-ray analyzer. The resulting iron value, as mass (e.g., micrograms), is divided by the amount of liquid which has passed through the filter as detected by the flow totalizer. The resulting calculation yields the part per billion level of iron in the liquid stream when iron mass is given in micrograms (mg) and flow total is given in liters.

(b) In the manner described above in Example 1 (*a*), water containing iron particles was passed through the filter in the average amount of 2 liters in every five minutes. The filter removed the iron containing particulates from the water sample. Removal of the water occurred by flushing with dry air or helium in 0.5 to 3 min. Iron was detected as 1.1 micrograms per liter (or ppb).

EXAMPLE 2

SULFUR DETERMINATION (a) The experiment for monitoring other elements contained in particulates, e.g., sulfur in a aqueous stream is exactly analogous to Example 1 (*a*) and Example 1 (*b*) described above for iron, except that the appropriate X-ray source and detector are used and the proper calibration has been performed.

(b) Similarly, in the manner described in Examples 1(*a*) and 1(*b*) and 2(*a*), the sulfur present is determined excepted that X-ray fluorescence date are detected using a sulfur probe and detector.

(c) Similarly in the manner described above in Example 2(*b*), other elements such as cobalt, nickel, tin or vanadium present as determined using the appropriate excitation probe and detector.

EXAMPLE 3

FIELD TEST

In one field test of the method, the monitor was connected to the feedwater line of a boiling water reactor (BWR) type power station to determine particulate iron levels on line. In a typical test, the sample flow rate was 400 milliliters per minute, sample collection time was 5 minutes, the chamber was flushed with air or helium gas, periodically at about 35–40 psig for about 0.1 to 3 min. and the X-ray scan time was five minutes. Repetitions of this test cycle continued for hours. The iron content of the sample stream was determined to be relatively steady over that time period and averaged 1.1 ppb. Results from the subject method compared favorably with two alternative measurement techniques: laboratory X-ray analysis and atomic absorption analysis.

While only a few embodiments of the invention have been shown and described herein, it will become apparent to those skilled in the art that various modifications and changes can be made in the apparatus or the method to determine particulate analyte in a moving liquid without departing from the spirit and scope of the present invention. All such modifications and changes coming within the scope of the appended claims are intended to be carried out hereby.

We claim:

1. An apparatus for the determination of the concentration level of a particulate analyte in a moving liquid, said apparatus comprising:

valve means for diverting a quantifiable portion of said liquid through an analysis chamber, wherein said chamber itself comprises:

valve inlet means for introducing the liquid to the analysis chamber, concentrating means for accumulating the particulate analyte present in the liquid, valve outlet means for the removing liquid having a reduced concentration of analyte;

valve inlet means for introducing an anhydrous gas into said analysis chamber, valve outlet means for removing the gas and a major portion of the liquid present in analysis chamber, x-ray radiation generating means positioned in non contacting proximity to said concentration means, detecting means for detecting an electromagnetic radiation parameter of the analyte located in non-contacting proximity to said concentration means, wherein the radiation is directed toward the concentration means and the detector means is positioned to receive the radiation after interaction with the concentration means; and flow sensor means for measuring the liquid flow within the analysis chamber.

2. The apparatus of claim 1 wherein the liquid is selected from water, one or more organic liquids, or combinations thereof.

3. The apparatus of claim 2 wherein the liquid concentration means is selected from an ion exchange membrane or a filter.

4. The apparatus of claim 3 wherein the liquid comprises water.

5. The apparatus of claim 4 wherein the anhydrous gas is selected from air, nitrogen, hydrogen, or combinations thereof.

6. The apparatus of claim 5 wherein the particulate analyte is selected from a metal, a metal compound a solid non metal, or a solid non metal compound.

7. The apparatus of claim 1 wherein the liquid to be sampled comprises water, the concentrating means is selected from a microfilter membrane or an ion exchange membrane, the anhydrous gas is selected from nitrogen, helium or combinations thereof, and the particulate analyte is selected from iron, sulfur or combinations thereof.

8. The apparatus of claim 7 wherein p1 the liquid consists essentially of water, and the concentration means is a microfilter membrane having a maximum pore size of about 0.45 microns.

9. The apparatus of claim 8 wherein the concentration of the particulate analyte in the liquid fluid is concentrated more than 10 times in the analysis chamber to obtain a particulate sample to analyze.

10. The apparatus of claim 9 wherein the analyte is iron and the lowest level of the particulate analyte in the concentrated sample which can be determined is about 1 part per billion.

11. A method for the determination of the concentration level of a particulate analyte in a moving liquid, said method comprising:

a. obtaining an apparatus itself comprising:

valve means for diverting a quantifiable portion of said liquid through an analysis chamber, wherein said chamber itself comprises:

valve inlet means for introducing the liquid to the analysis chamber, concentrating means for accumulating the particulate analyte present in the liquid, valve outlet means for removing the liquid having a reduced concentration of analyte;

valve inlet means for introducing an anhydrous gas into said analysis chamber, valve outlet means for removing the inert gas and a major portion of the liquid present in the analysis chamber, x-ray radiation generating means positioned in non contacting proximity to said concentration means, detecting means for detecting of an electromagnetic radiation parameter located in non-contacting proximity to said concentration means, wherein the radiation is directed toward the concentration means and the detector means is positioned to receive the radiation after interaction with the concentration means; and optional flow sensor means for measuring the liquid flow within the analysis chamber;

b. diverting a quantifiable portion of the moving liquid into the analysis chamber;

c. concentrating the particulate analyte for a period of time using said concentration means;

d. contacting the concentrated analyte with an gas via the valve inlet means to remove the liquid present in the analysis chamber via the valve outlet;

e. irradiating the concentrated analyte in the analysis chamber with electromagnetic radiation;

f. detecting and quantifying an electromagnetic radiation parameter of the analyte; and g. correlating the electromagnetic radiation parameter of the analyte with a predetermined scale of values to determine the concentration of the particulate analyte in the moving liquid.

12. The method of claim 11 wherein the liquid is selected from water, one or more organic liquids, or combinations thereof.

13. The method of claim 12 wherein the concentration means is selected from an ion exchange membrane or a filter.

14. The method of claim 13 wherein the liquid comprises water.

15. The method of claim 14 wherein the anhydrous gas is selected from air, nitrogen, helium, or combinations thereof.

16. The method of claim 15 wherein the particulate analyte is selected from a metal, a metal compound, a solid non metal, or a solid non metal compound.

17. The method of claim 11 wherein the liquid to be sampled comprises water, the concentrating means is selected from a microfilter membrane or an ion exchange membrane, the anhydrous gas is selected from nitrogen, helium or combinations thereof, and the particulate analyte is selected from iron, iron compounds, sulfur, sulfur compounds or combinations thereof.

18. The method of claim 17 wherein the liquid consists essentially of water, and the concentration means is a microfilter membrane having a maximum pore size of about 0.45 microns.

19. The method of claim 18 wherein the concentration of the particulate analyte in the feed liquid is concentrated more than 1000 times in the analysis chamber to obtain a particulate sample to analyze.

20. The method of claim 19 wherein the analyte is iron and the lowest level of the particulate analyte in the concentrated sample which can be determined is about 1 part per billion iron.

* * * * *